United States Patent
Furo et al.

(10) Patent No.: US 10,595,528 B2
(45) Date of Patent: Mar. 24, 2020

(54) LIQUID SPRAY AGENT FOR AGRICULTURAL USE

(71) Applicant: THE NIPPON SYNTHETIC CHEMICAL INDUSTRY CO., LTD., Osaka (JP)

(72) Inventors: Chizuko Furo, Osaka (JP); Shusaku Mandai, Osaka (JP)

(73) Assignee: MITSUBISHI CHEMICAL CORPORATION, Tokyo (JP)

(*) Notice: Subject to any disclaimer, the term of this patent is extended or adjusted under 35 U.S.C. 154(b) by 81 days.

(21) Appl. No.: 15/031,029

(22) PCT Filed: Dec. 11, 2014

(86) PCT No.: PCT/JP2014/082779
§ 371 (c)(1),
(2) Date: Apr. 21, 2016

(87) PCT Pub. No.: WO2015/093380
PCT Pub. Date: Jun. 25, 2015

(65) Prior Publication Data
US 2016/0262381 A1 Sep. 15, 2016

(30) Foreign Application Priority Data
Dec. 20, 2013 (JP) ................................. 2013-263672

(51) Int. Cl.
*A01N 25/24* (2006.01)
*C05G 3/02* (2006.01)
*A01N 25/10* (2006.01)
*A01N 25/02* (2006.01)

(52) U.S. Cl.
CPC .............. *A01N 25/24* (2013.01); *A01N 25/02* (2013.01); *A01N 25/10* (2013.01); *C05G 3/02* (2013.01)

(58) Field of Classification Search
CPC ........ A01N 25/24; A01N 25/02; A01N 25/10; C05G 3/04
See application file for complete search history.

(56) References Cited

U.S. PATENT DOCUMENTS

| 3,591,360 A * | 7/1971 | Vahlsing ............... A01N 59/00 504/163 |
| 5,674,514 A | 10/1997 | Hasslin |
| 2008/0138312 A1* | 6/2008 | Kritzler ................. A01N 33/12 424/78.31 |
| 2013/0053244 A1* | 2/2013 | Devisetty ............... A01N 37/42 504/136 |

FOREIGN PATENT DOCUMENTS

| CN | 1114855 A | 1/1996 |
| CN | 101111150 A | 1/2008 |
| JP | 08-217604 | 8/1996 |
| JP | 2012-006881 A | 1/2012 |
| WO | 2006/081617 A | 8/2006 |

OTHER PUBLICATIONS

International Search Report issued in PCT/JP2014/082779, dated Feb. 10, 2015.
International Preliminary Report on Patentability issued in PCT/JP2014/082779, dated Jun. 30, 2016.
Extended European Search Report in European Application No. 14872288.7, dated Jun. 30, 2017.
CN OA issued in CN Patent App. No. 201480063499.9 (dated Jun. 4, 2019) w/ English translation.
CN OA (dated Sep. 10, 2019) issued for CN Patent Application No. 201480063499.9 w/ Eng. translation.
"Speader," "sticker," stabilizer, Concise Pesticide Dictionary, p. 64, Chemical Industry Press Oct. 1985.
Foreign Patent Abstract—Fertilizer, p. 35, Nov. 1977.

* cited by examiner

*Primary Examiner* — John Pak
*Assistant Examiner* — Nathan W Schlientz
(74) *Attorney, Agent, or Firm* — Greenblum & Bernstein, P.L.C.

(57) ABSTRACT

Provided is a liquid spray agent for agricultural use, including a polyvinyl alcohol-based resin having a saponification degree of from 30 mol %, to 60 mol %. With this, a liquid spray agent for agricultural use, which is used in agricultural and horticultural fields and has high fixation ability and excellent sprayability, can be provided.

4 Claims, No Drawings

LIQUID SPRAY AGENT FOR AGRICULTURAL USE

TECHNICAL FIELD

The embodiment of the present invention relates to a liquid spray agent for agricultural use including an active component excellent in fixation ability.

BACKGROUND ART

In general, in agricultural and horticultural fields, a fertilizer for growth promotion of fruits, vegetables, and the like or an agricultural chemical for extermination of pests is diluted with water and sprayed with no additives. However, when the fertilizer or agricultural chemical is diluted with water and sprayed onto plants with no additives, an active component of the fertilizer or agricultural chemical runs off due to rainfall or the like or is released or detached due to wind, which may often impair sustentation of effects.

Accordingly, in order to improve adhesion ability or fixation ability of the active component in the fertilizer or agricultural chemical to a plant, a spreading agent is usually added to a solution obtained by diluting the fertilizer or agricultural chemical with water. As the spreading agent, for example, there is generally used a polyoxyethylene alkyl phenyl ether, a polyoxyethylene alkyl ether, a polyoxyethylene fatty acid ester, a lignin sulfonate, or a naphthylmethanesulfonate, which has a property of reducing the surface tension of a spray liquid to improve adhesion ability or spreadability to a hardly wetted mite's body or crop plant and to enhance an effect of the fertilizer or agricultural chemical. However, the agents have very high affinity to water, and hence the runoff of the agents due to rainfall cannot be suppressed.

Some of spreading agents exhibiting fixation effects contain a polyoxyethylene resin acid ester, paraffin, or the like as a major component, but have problems in that the effects of the agents cannot be exhibited when the agents are used at low concentrations, and in that films formed by drying the agents are not dissolved in water and hence remain forever on plants. The spreading agents further have problems in that the agents are poorly soluble in the above-mentioned solutions diluted with water and act only when blended in large amounts.

In recent years, a fixable composition of an agrochemical active component containing a polyvinyl alcohol has been developed to solve the above-mentioned problems (see Patent Document 1).

RELATED ART DOCUMENT

Patent Document

PTL 1: JP-A-HEI8 (1996)-217604

SUMMARY OF INVENTION

However, in Patent Document 1, there is disclosed that the polyvinyl alcohol used in the fixable composition has a saponification degree of preferably from 71 mol % to 89 mol % from the viewpoint of water solubility. The saponification degree falls within a range of saponification degrees of generally commercially available partially saponified polyvinyl alcohols, and the polyvinyl alcohol has room for improvement in fixation ability.

In addition, a chemical such as a fertilizer, an agricultural chemical, a herbicide, or an insect repellent is added to a liquid spray agent used in agricultural and horticultural fields as a chemical from which an active component of the agent is derived. However, many of the chemicals have a property of being poorly soluble in water, and, in many cases, may be excellent in solubility in a solvent containing an adequate amount of an alcohol. However, when a polyvinyl alcohol is blended in an alcohol, aggregates may be formed to impair sprayability. Accordingly, there has been required a liquid spray agent for agricultural use that maintains sprayability even when an alcohol is used in a solvent, and is excellent in fixation ability.

The embodiment of the present invention has been made in view of such circumstances, and an object of the embodiment of the present invention is to provide a liquid spray agent for agricultural use, which is used in agricultural and horticultural fields and has high fixation ability and excellent sprayability.

The inventors of the embodiment of the present invention have made extensive investigations in view of such circumstances, and as a result, have found that, when a liquid spray agent for agricultural use is produced so as to contain a polyvinyl alcohol having a saponification degree of from 30 mol % to 60 mol %, the agent is excellent in fixation ability and has sprayability that is not deteriorated even when an alcohol is used in a solvent. Thus, the embodiment of the present invention has been completed.

That is, the embodiment of the present invention relates to a liquid spray agent for agricultural use, including a polyvinyl alcohol-based resin having a saponification degree of from 30 mol % to 60 mol %.

It should be noted that the polyvinyl alcohol-based resin used in the embodiment of the present invention has a low saponification degree as mentioned above, and hence is also referred to as vinyl ester-based resin.

The liquid spray agent for agricultural use of the embodiment of the present invention is excellent in sprayability as well as fixation ability because of the effect of a specific polyvinyl alcohol-based resin in the agent. In addition, even when an adequate amount of an alcohol is used in a solvent, the agent does not form aggregates and can have high sprayability. Accordingly, even when an agricultural chemical or the like having a property of being poorly soluble in water and readily soluble in an alcohol is blended in the agent, the resultant can be satisfactorily used as a spray agent. In particular, the liquid spray agent for agricultural use of the embodiment of the present invention is preferably used as a spray agent for foliar application.

DESCRIPTION of EMBODIMENTS

The following descriptions on constituent features are examples (typical examples) of embodiments of the present invention, and the embodiment of the present invention is not limited to the descriptions.

The embodiment of the present invention is described below in detail.

As described above, a liquid spray agent for agricultural use of the embodiment of the present invention has a feature of containing a polyvinyl alcohol-based resin having a saponification degree of from 30 mol % to 60 mol % (The resin is hereinafter abbreviated as "specific PVA-based resin." The polyvinyl alcohol is abbreviated as "PVA"). The saponification degree of the specific PVA-based resin is preferably from 30 mol % to 60 mol %, more preferably 33 mol % to 50 mol %.

This is because, when the saponification degree is too low, the agent becomes insoluble in water and does not act as a water-soluble spray agent, while when the saponification degree is too high, the agent tends to have lowered fixation ability and lowered sprayability due to an aggregation reaction with an alcohol. It should be noted that the saponification degree can be determined by an analysis based on alkali consumption required for hydrolysis of residual vinyl acetate.

The specific PVA-based resin can be usually obtained by partially saponifying a vinyl ester-based polymer prepared by polymerization of a vinyl ester-based compound.

As the vinyl ester-based compound, for example, vinyl formate, vinyl acetate, vinyl trifluoroacetate, vinyl propionate, vinyl butyrate, vinyl caprate, vinyl laurate, a vinyl versatate, vinyl palmitate, vinyl stearate, or pivalic acid is used alone, or two or more kinds thereof are used in combination. It should be noted that in practical use, vinyl acetate is preferably used from the viewpoint of cost effectiveness.

In addition, the specific PVA-based resin may be an unmodified one or a modified one. In particular, the modified PVA-based resin has high affinity to an alcohol, and hence is preferably used when an alcohol is added to a solvent for the liquid spray agent for agricultural use.

The modified PVA can be produced by saponifying a polymer of a vinyl ester-based monomer and another unsaturated monomer, or by post-modifying PVA.

Examples of the "other unsaturated monomer" include: olefins, such as ethylene, propylene, isobutylene, α-octene, α-dodecene, and α-octadecene; unsaturated acids, such as acrylic acid, methacrylic acid, crotonic acid, maleic acid, maleic anhydride, and itaconic acid, or salts or monoalkyl or dialkyl esters thereof; nitriles, such as acrylonitrile and methacrylonitrile; amides, such as acrylamide or methacrylamide; olefinsulfonic acids, such as ethylenesulfonic acid, allylsulfonic acid, and methallylsulfonic acid, or salts thereof; alkyl vinyl ethers; N-acrylamidomethyltrimethylammonium chloride; allyltrimethylammonium chloride; dimethylallyl vinyl ketone; N-vinylpyrrolidone; vinyl chloride; vinylidene chloride; polyoxyalkylene (meth)allyl ethers, such as polyoxyethylene (meth)allyl ether and polyoxypropylene (meth)allyl ether; polyoxyalkylene (meth) acrylates, such as polyoxyethylene (meth)acrylate and polyoxypropylene (meth)acrylate; polyoxyalkylene (meth) acrylamides, such as polyoxyethylene (meth) acrylamide and polyoxypropylene (meth) acrylamide; and polyoxyethylene (1-(meth)acrylamido-1,1-dimethylpropyl) ester, polyoxyethylene vinyl ether, polyoxypropylene vinyl ether, polyoxyethylene allyl amine, polyoxypropylene allyl amine, polyoxyethylene vinyl amine, and polyoxypropylene vinyl amine.

In addition, as a method for the post-modification, there is given, for example, a method involving acetoacetic acid esterification, acetalization, urethanization, etherification, grafting, phosphoric acid esterification, or oxyalkylenation of PVA.

In addition, of the modified PVAs, anionically modified PVA or nonionically modified PVA is particularly preferred from the viewpoint of its high affinity to water. Examples of the anionically modified PVA include carboxyl group-containing PVA, sulfonic group-containing PVA, and phosphoric group-containing PVA. In addition, examples of the nonionically modified PVA include oxyalkylene group-containing PVA, acetoacetyl group-containing PVA, diacetone acrylamide-modified PVA, mercapto group-containing PVA, silanol group-containing PVA, and side-chain 1,2-diol structural unit-containing PVA. Of those, oxyalkylene group-containing PVA or carboxyl group-containing PVA is preferred from the viewpoint of solubility in an alcohol.

It should be noted that, in the liquid spray agent for agricultural use of the embodiment of the present invention, the modification rate of the modified PVA used is usually from 0.1 mol % to 10 mol %. In addition, the modification rate of the anionically modified PVA is preferably from 0.1 mol % to 1 mol %, particularly preferably from 0.2 mol % to 0.5 mol %, and the modification rate of the nonionically modified PVA is preferably from 0.5 mol % to 5 mol %, particularly preferably from 1 mol % to 2 mol %.

The specific PVA-based resin used in the liquid spray agent for agricultural use of the embodiment of the present invention usually has an average degree of polymerization (determined in conformity with JIS K 6726) of preferably from 100 to 2,000, particularly preferably from 150 to 1,000, more particularly preferably from 200 to 800. That is, this is because, when the average degree of polymerization of the PVA-based resin is too low, the agent has lowered fixation ability, while when the average degree of polymerization is too high, the agent has lowered solubility.

As a solvent used in the liquid spray agent for agricultural use of the embodiment of the present invention, there is given, for example, water or water containing an alcohol. In addition, when the water containing an alcohol, i.e., a water-alcohol mixed solvent is used, the mixing ratio (weight ratio) of water/alcohol is usually from 9/1 to 1/9, particularly preferably from 7/3 to 2/8, more particularly preferably from 6/4 to 3/7. This is because, when such solvent is used, the agent is excellent in sprayability, chemical solubility, quick drying ability (quick film forming ability), and the like.

In addition, the chemical used in the liquid spray agent for agricultural use of the embodiment of the present invention may be a chemical from which an active component of the agent is derived, i.e., a chemical required to have fixation ability to a plant, such as an agricultural chemical, a fertilizer, a herbicide, or an insect repellent. The chemical used may be any chemical as long as the chemical can be dissolved or dispersed in water or an alcohol, and is required to be inactive with the specific PVA-based resin used in the liquid spray agent for agricultural use of the embodiment of the present invention.

To the liquid spray agent for agricultural use of the embodiment of the present invention, there may be added the specific PVA-based resin, the solvent, and the chemical, and if necessary, another component such as an emulsifier, a wettable powder, a flowable, a surfactant, a thickener, or a preservative. It should be noted that the amount of the other component blended is preferably 10 wt % or less with respect to the whole of the liquid spray agent for agricultural use.

In this case, the liquid spray agent for agricultural use of the embodiment of the present invention can be prepared by a method involving: (1) mixing a solution of the specific PVA-based resin with a solution of the chemical; (2) adding a powdery chemical to a solution of the specific PVA-based resin solution and mixing the resultant; or (3) adding powder of the specific PVA-based resin to a solution of the chemical and mixing the resultant. Of those, the agent is preferably prepared by the method shown in the item (1).

The concentration of the specific PVA-based resin in the liquid spray agent for agricultural use of the embodiment of the present invention prepared as above is usually from 0.01 wt % to 30 wt %, preferably from 0.1 wt % to 20 wt %, more preferably from 1 wt % to 10 wt %. This is because, when the agent is prepared so as to contain the specific PVA-based resin at such concentration, the agent is excellent in fixation ability and sprayability.

In addition, the concentration of the chemical from which the active component is derived in the liquid spray agent for agricultural use of the embodiment of the present invention is usually from 0.1 ppm by weight to 5,000 ppm by weight, preferably from 1 ppm by weight to 1,000 ppm by weight, more preferably from 10 ppm by weight to 500 ppm by weight. This is because, when the agent is prepared so as to contain the chemical at such concentration, the active component in the chemical can act effectively.

In addition, the liquid spray agent for agricultural use of the embodiment of the present invention can be used as a spray agent for leaves, stems, or fruits, or an additive for a water culture medium or a feed solution. The agent is particularly preferably used as a spray agent for foliar application.

EXAMPLES

Next, the embodiment of the present invention is described in more detail. However, the embodiment of the present invention is not limited to the following Examples as long as the modification is true to the gist of the invention.

Example 1

<Preparation of PVA-Based Resin (1)>

1,000 parts by weight of vinyl acetate and 300 parts by weight of methanol were loaded into a reaction vessel equipped with a reflux condenser, a drip funnel, and a stirrer, and azobisisobutyronitrile was added thereto at 0.079 mol % (with respect to vinyl acetate loaded), and the temperature was raised with stirring in a nitrogen stream to start polymerization. 2 hours and 4 hours after the start of polymerization, azobisisobutyronitrile was added thereto at 0.079 mol % (with respect to vinyl acetate loaded), and at the time point when the polymerization ratio of vinyl acetate reached 94%, a predetermined amount of m-dinitrobenzene was further added to complete the polymerization. Subsequently, unreacted vinyl acetate monomers were removed from the system by distillation while blowing methanol steam thereinto. Thus, a solution of a copolymer in methanol was obtained.

Subsequently, the methanol solution was adjusted so as to contain the copolymer at a concentration of 50% and loaded into a kneader, and saponification was carried out by adding a solution of 2% sodium hydroxide in methanol at a ratio of 10 mmol with respect to 1 mol of a vinyl acetate structural unit in the copolymer while the temperature of the solution was maintained at 40° C. At the time when a saponified product was precipitated to form particles with progression of saponification, acetic acid for neutralization was added in an amount of 0.8 equivalent relative to sodium hydroxide, and the mixture was filtered. The residue was washed with methanol well and dried in a hot-air dryer. Thus, an unmodified PVA-based resin [PVA-based resin (1)] was obtained.

The resultant PVA-based resin (1) was found to have a saponification degree, as determined by an analysis based on alkali consumption required for hydrolysis of residual vinyl acetate, of 49 mol %, and an average degree of polymerization, as determined by an analysis in conformity with JIS K 6726, of 250.

The PVA-based resin (1) obtained as above was dissolved in a mixed solvent having a water/ethanol ratio (weight ratio) of 6/4 to prepare a solution containing PVA at a concentration of 5 wt %. Then, a non-alcohol-based liquid fertilizer (manufactured by HYPONeX JAPAN CORP., LTD., HYPONEX) was diluted to a predetermined concentration, and 5 parts by weight of the diluted solution was added to 100 parts by weight of the PVA solution. Thus, a liquid spray agent for agricultural use was prepared.

Example 2

An unmodified PVA-based resin having a saponification degree of 34 mol % and an average degree of polymerization of 300 was prepared in conformity with the method of preparing the PVA-based resin (1). Then, a liquid spray agent for agricultural use was prepared in the same manner as in Example 1 except that the unmodified PVA-based resin prepared as above was used instead of the PVA-based resin (1).

Example 3

<Preparation of PVA-Based Resin (2)>

1,000 parts by weight of vinyl acetate, 9,580 parts by weight of methanol, and 237 parts by weight (2 mol % with respect to vinyl acetate loaded) of polyoxyethylene allyl ether having an average chain length of n=10 were loaded into a reaction vessel equipped with a reflux condenser, a drip funnel, and a stirrer, and azobisisobutyronitrile was added thereto at 0.079 mol % (with respect to vinyl acetate loaded), and the temperature was raised with stirring in a nitrogen stream to start polymerization. Further, 1,410 parts by weight of vinyl acetate, 3,195 parts by weight of methanol, and 2,130 parts by weight of polyoxyethylene allyl ether were added dropwise thereto over 13 hours, and 4 hours after the start of polymerization, azobisisobutyronitrile was further added thereto at 0.079 mol % (with respect to vinyl acetate loaded). At the time when the polymerization ratio of vinyl acetate reached 94%, a predetermined amount of m-dinitrobenzene was added to complete the polymerization, and unreacted vinyl acetate monomers were removed from the system by distillation while blowing methanol steam thereinto. Thus, a solution of a copolymer in methanol was obtained.

Subsequently, the methanol solution was adjusted so as to contain the copolymer at a concentration of 40% and loaded into a kneader, and saponification was carried out for 1.5 hours by adding a solution of 2% sodium hydroxide in methanol at a ratio of 10 mmol with respect to 1 mol of a vinyl acetate structural unit in the copolymer while the temperature of the solution was maintained at 40° C. Acetic acid for neutralization was added thereto in an amount of 0.8 equivalent relative to sodium hydroxide, and the mixture was heated with stirring to remove methanol completely. Subsequently, water was added to dissolve the resultant. Thus, a 40% aqueous solution of an oxyalkylene group-containing PVA-based resin [PVA-based resin (2)] was obtained.

The resultant PVA-based resin (2) was found to have a saponification degree, as determined by an analysis based on alkali consumption required for hydrolysis of residual vinyl acetate, of 48 mol %, and an average degree of polymerization, as determined by an analysis in conformity with JIS K 6726, of 260. In addition, the PVA-based resin (2) had a modification ratio [oxyalkylene group content], determined based on the load amount, of 1.8 mol %.

A liquid spray agent for agricultural use was prepared in the same manner as in Example 1 except that the PVA-based resin (2) obtained as above was used

Example 4

An oxyalkylene group-containing PVA-based resin having a saponification degree of 43 mol %, an average degree of polymerization of 280, and a modification ratio of 1.7 mol % was prepared in conformity with the method of preparing the PVA-based resin (2). Then, a liquid spray agent for agricultural use was prepared in the same manner as in Example 1 except that the modified PVA-based resin prepared as above was used instead of the PVA-based resin (1).

Example 5

<Preparation of PVA-Based Resin (3)>

Vinyl acetate and 3-mercaptopropionic acid were copolymerized in methanol. The resultant copolymer was saponified with sodium hydroxide.

The resultant PVA-based resin (3) was found to have a saponification degree, as determined by an analysis based on alkali consumption required for hydrolysis of residual vinyl acetate, of 38 mol %, and an average degree of polymerization, as determined by an analysis in conformity with JIS K 6726, of 530. In addition, the PVA-based resin (3) had a modification ratio [terminal carboxyl group content], determined based on the load amount, of 0.25 mol %. When the resultant PVA-based resin (3) was purified by 48-hour Soxhlet extraction with methanol, dissolved in heavy water, and subjected to a nuclear magnetic resonance analysis (hereinafter abbreviated as NMR), the PVA-based resin (3) was found to have a COONa group at the end of its molecule, which suggested that the PVA-based resin (3) had a carboxyl group represented by $NaOOC-CH_2-CH_2-S-$ at the one end of the molecule.

A liquid spray agent for agricultural use was prepared in the same manner as in Example 1 except that the PVA-based resin (3) obtained as above was used instead of the PVA-based resin (1).

Comparative Example 1

An unmodified PVA-based resin having a saponification degree of 80 mol % and an average degree of polymerization of 350 was prepared in conformity with the method of preparing the PVA-based resin (1). Then, a liquid spray agent for agricultural use was prepared in the same manner as in Example 1 except that the unmodified PVA-based resin prepared as above was used instead of the PVA-based resin (1) and the water/ethanol ratio (weight ratio) of the water/ethanol mixed solvent was changed to 9/1.

Comparative Example 2

An unmodified PVA-based resin having a saponification degree of 88 mol % and an average degree of polymerization of 600 was prepared in conformity with the method of preparing the PVA-based resin (1). Then, a liquid spray agent for agricultural use was prepared in the same manner as in Example 1 except that the unmodified PVA-based resin prepared as above was used instead of the PVA-based resin (1) and the water/ethanol ratio (weight ratio) of the water/ethanol mixed solvent was changed to 9/1.

The liquid spray agents for agricultural use obtained as above in Examples and Comparative Examples were evaluated for fixation ability according to the following criteria. The results are collectively shown in Table 1 below.

<<Evaluation of Fixation Ability>>

0.1 part by weight of a coloring (red food coloring) was added to 105 parts by weight of a liquid spray agent for agricultural use, and then the liquid spray agent for agricultural use was sprayed on the leaf surfaces of a plant (Benjamin) using a spray. The plant was allowed to stand still for 24 hours, and then water was sprayed on the leaf surfaces (the surfaces on which the liquid spray agent for agricultural use was sprayed) of the plant using a spray. Then, the remaining colored leaf surfaces were visually observed, and a plant having colored leaf surfaces remaining at a ratio of 80% or more with respect to the area of the leaf surfaces (the surfaces on which the liquid spray agent for agricultural use was sprayed) was evaluated as "o". It should be noted that a plant having colored leaf surfaces remaining at a ratio of 30% or more and less than 60% with respect to the area of the leaf surfaces (the surfaces on which the liquid spray agent for agricultural use was sprayed) was evaluated as "Δ", and a plant having colored leaf surfaces remaining at a ratio of less than 30% with respect to the area of the leaf surfaces was evaluated as "x".

TABLE 1

| | PVA-based resin | | | | | Evaluation of fixation ability |
|---|---|---|---|---|---|---|
| | Saponification degree (mol %) | Average degree of polymerization | Type of modification | Modification ratio (mol %) | Water/ethanol | |
| Example 1 | 49 | 250 | Unmodified | — | 6/4 | o |
| Example 2 | 34 | 300 | Unmodified | — | 6/4 | o |
| Example 3 | 48 | 260 | Oxyalkylene | 1.8 | 6/4 | o |
| Example 4 | 43 | 280 | Oxyalkylene | 1.7 | 6/4 | o |
| Example 5 | 38 | 530 | Terminal carboxyl group | 0.25 | 6/4 | o |
| Comparative Example 1 | 80 | 350 | Unmodified | — | 9/1 | Δ |
| Comparative Example 2 | 88 | 600 | Unmodified | — | 9/1 | x |

The results shown in Table 1 above reveal that the liquid spray agents for agricultural use of Examples have high fixation ability and are excellent in sprayability because the agents are sprayed uniformly on leaf surfaces. On the other hand, the liquid spray agents for agricultural use of Comparative Examples were prepared using the mixed solvent having a water/ethanol ratio (weight ratio) of 9/1 because in the case of using the mixed solvent having a water/ethanol ratio (weight ratio) of 6/4, the PVA-based resin was not dissolved in the solvent and the agents could not be sprayed and evaluated for fixation ability. However, such liquid spray agents were found to be inferior in fixation ability as compared to those of Examples.

In addition, the liquid spray agents for agricultural use of Examples and Comparative Examples were evaluated for solubility according to the following criteria. The results are collectively shown in Table 2 below.

<<Evaluation of Solubility>>

The PVA-based resins of Examples and Comparative Examples were mixed in solvents containing water and ethanol at the following ratios (weight ratios) at a concentration of 5% at room temperature, and solubility behavior was observed with stirring according to the following criteria A to C.

A: Dissolved
B: Not dissolved (stably dispersed)
C: Not dissolved (dispersed and then precipitated)

TABLE 2

| | Water/ethanol (weight ratio) | | | | | | | | | | |
|---|---|---|---|---|---|---|---|---|---|---|---|
| | 10/0 | 9/1 | 8/2 | 7/3 | 6/4 | 5/5 | 4/6 | 3/7 | 2/8 | 1/9 | 0/10 |
| Example 1 | C | C | C | C | B | A | A | A | A | A | A |
| Example 2 | C | C | C | B | A | A | A | A | A | A | A |
| Example 3 | B | B | B | A | A | A | A | A | A | A | A |
| Example 4 | B | B | B | B | A | A | A | A | A | A | A |
| Example 5 | B | B | B | B | B | A | A | A | A | A | A |
| Comparative Example 1 | A | A | C | C | C | C | C | C | C | C | C |
| Comparative Example 2 | A | A | C | C | C | C | C | C | C | C | C |

The results shown in Table 2 above reveal that the PVA-based resins of Examples were dissolved or dispersed in a wide range of water/alcohol mixing ratios as compared to the PVA-based resins of Comparative Examples. In particular, the modified PVA-based resins of Examples 3 to 5 were dissolved or dispersed in a wider range of water/alcohol mixing ratios.

It should be noted that, even when a PVA-based resin having a saponification degree of about 25 mol % is to be dissolved in a solvent containing water alone, the PVA-based resin is considered not to be dissolved and not to act as a water-soluble spray agent.

Specific modes in the embodiment of the present invention have been shown in Examples above, but such Examples are purely illustrative and are not to be interpreted as limiting the embodiment of the present invention. Various modifications apparent to a person skilled in the art are intended to fall within the scope of the embodiment of the present invention.

The liquid spray agent for agricultural use of the embodiment of the present invention has high fixation ability and is excellent in sprayability because of the effect of a specific PVA-based resin in the agent. Accordingly, the agent is effectively applied to a liquid spray agent to be used in agricultural and horticultural fields, for example, a spray agent for leaves, stems, and fruits.

The invention claimed is:

1. A liquid spray agent for agricultural use, comprising a polyvinyl alcohol resin having a saponification degree of from 30 mol % to 50 mol % and an average degree of polymerization of from 100 to 2,000; and further comprising a fertilizer, an herbicide, or an insect repellent.

2. The liquid spray agent for agricultural use according to claim 1, wherein the polyvinyl alcohol resin comprises unmodified polyvinyl alcohol, carboxyl group-containing PVA, sulfonic group-containing PVA, phosphoric group-containing PVA, oxyalkylene group-containing PVA, acetoacetyl group-containing PVA, diacetone acrylamide-modified PVA, mercapto group-containing PVA, silanol group-containing PVA, or side-chain 1,2-diol structural unit-containing PVA.

3. The liquid spray agent for agricultural use according to claim 1, further comprising, as a solvent, water containing an alcohol.

4. The liquid spray agent for agricultural use according to claim 1, wherein the liquid spray agent for agricultural use further comprises a spray agent for foliar application.

* * * * *